United States Patent
Kale et al.

(10) Patent No.: US 10,605,756 B2
(45) Date of Patent: Mar. 31, 2020

(54) SYSTEM AND METHOD OF DETECTING EXPLOSIVE COMPOUNDS BASED ON RAPID DEFLAGRATION AND DIFFERENTIAL MICRO-CALORIMETRY

(71) Applicant: Nanosniff Technologies Pvt. Ltd., Mumbai (IN)

(72) Inventors: Nitin S Kale, Mumbai (IN); Nehul Gullaiya, Mumbai (IN); Deepali Chandratre, Mumbai (IN); Sachin Sangave, Mumbai (IN); Hrishikesh Desai, Mumbai (IN); V Ramgopal Rao, Mumbai (IN); Soumyo Mukherji, Mumbai (IN); Kapil Bardeja, Mumbai (IN)

( * ) Notice: Subject to any disclaimer, the term of this patent is extended or adjusted under 35 U.S.C. 154(b) by 316 days.

(21) Appl. No.: 15/554,448

(22) PCT Filed: Mar. 3, 2016

(86) PCT No.: PCT/IN2016/050074
§ 371 (c)(1),
(2) Date: Aug. 30, 2017

(87) PCT Pub. No.: WO2017/051430
PCT Pub. Date: Mar. 30, 2017

(65) Prior Publication Data
US 2018/0067067 A1    Mar. 8, 2018

(30) Foreign Application Priority Data
Mar. 5, 2015 (IN) .......................... 738/MUM/2015

(51) Int. Cl.
*G01N 27/18* (2006.01)
*G01N 1/44* (2006.01)
(Continued)

(52) U.S. Cl.
CPC ............. *G01N 27/18* (2013.01); *G01N 1/44* (2013.01); *G01N 33/227* (2013.01); *G01N 2001/028* (2013.01)

(58) Field of Classification Search
CPC ...... G01N 27/18; G01N 33/227; G01N 25/50; G01N 25/52; G01N 33/22; G01M 99/002
(Continued)

(56) References Cited

U.S. PATENT DOCUMENTS 5,057,436 A * 10/1991 Ball .................. G01N 33/0031
                                                    436/113
6,367,970 B1 * 4/2002 Danielson .............. G01K 13/02
                                                    374/179
(Continued)

*Primary Examiner* — Gail Kaplan Verbitsky
(74) *Attorney, Agent, or Firm* — The Law Office of Austin Bonderer, PC; Austin Bonderer

(57) ABSTRACT

An explosive detection system for detecting explosive trace in a sample includes a detection unit, and a processing unit. The detection unit that receives a desorbed sample includes a first heater, a second heater, a first resistance temperature detector (RTD), a second RTD, and an amplifier. The first heater is exposed to the desorbed sample. The first heater and the second heater are supplied with specific voltage for three or more experiments. The first RTD and the second RTD measure changes in resistance due to heating of the first heater and the second heater to calculate voltages across the first RTD and the second RTD. The amplifier amplifies the voltages to calculate a differential voltage for each of the three or more experiments, and converts the differential voltage into a digital signal. The processing unit is configured to process the digital signal to detect explosive trace in the desorbed sample.

10 Claims, 11 Drawing Sheets

(51) Int. Cl.
*G01N 33/22* (2006.01)
*G01N 1/02* (2006.01)

(58) Field of Classification Search
USPC .............. 374/8, 31–39, 1, 185, 163, 5, 45; 422/51; 436/147
See application file for complete search history.

(56) References Cited

U.S. PATENT DOCUMENTS

| | | | |
|---|---|---|---|
| 6,471,507 B1* | 10/2002 | Hall | F23D 14/28 |
| | | | 374/8 |
| 8,201,992 B2* | 6/2012 | Horovitz | G01N 27/123 |
| | | | 374/16 |
| 8,292,496 B1* | 10/2012 | Fine | G01N 33/227 |
| | | | 374/8 |
| 9,702,861 B2* | 7/2017 | Adams | G01N 25/00 |
| 2011/0024617 A1* | 2/2011 | Neidholdt | H01J 49/10 |
| | | | 250/282 |

* cited by examiner

SYSTEM AND METHOD OF DETECTING EXPLOSIVE COMPOUNDS BASED ON RAPID DEFLAGRATION AND DIFFERENTIAL MICRO-CALORIMETRY

CROSS-REFERENCE TO RELATED APPLICATIONS

This application claims priority from PCT Patent Application number PCT/IN2016/050074 filed on Mar. 3, 2016 the complete disclosure of which, in its entirely, is herein incorporated by reference

BACKGROUND

Technical Field

The embodiments herein generally relate to a system for detecting explosive traces, and, more particularly, to a system and method of detecting explosive traces based on rapid deflagration and differential micro-calorimetry.

Description of the Related Art

An explosive material, also called an explosive, is a reactive substance that contains a great amount of potential energy that can produce an explosion if released suddenly, usually accompanied by the production of light, heat, sound, and pressure. The explosives are very sticky substances. The explosives tend to stick on to various objects, body-parts, clothes, etc. Being very sticky in nature, the explosive traces do not tend to leave the initial surface of rest easily. If such objects are swiped and analyzed, the explosive traces can be collected. However, collection of these particles/vapors is a difficult task, and needs to be addressed through novel engineering approaches. The explosive traces can be removed from the surface only by applying additional force/energy. The explosive traces have very low vapor pressure at room temperature, therefore one cannot easily smell the explosive traces to detect it. Combating the surge in explosives-based terrorism requires cost effective explosive sensors that are highly selective and extremely sensitive.

Existing technologies used for detection of explosive traces are based on direct air sampling of explosive vapors surrounding the found explosive contraband or particulate sampling technique. The direct air sampling is effective only for sufficiently volatile explosive components, while the explosive components, mostly used for creation of so called plastic explosives feature very low or zero volatility at ambient temperature.

There is a great demand world-wide for reliable detection technologies, being capable to sample and detect all kinds of explosive compounds. Most of the existing detection technologies use an IMS (Ion Mobility Spectrometry) detection principle, or other technologies, focused for direct identification of the sample; unfortunately, those detection principles are very sensitive for cross-talks by various disturbing chemicals and saturation due to very limited dynamic range. Both above limitations create potentially high false alarm rate and causes moreover a number of serious problems with after-exposure cleaning of the system.

The existing portable systems work mostly in the cycle "sampling—pre-concentration—analyses". This operation cycle requires the operator to sample just from one spot to the found traces. There is no indication about the properly selected spot during the sampling interval, so the operator may sample from the improper spot or location, while losing a valid operational time.

Most of the existing systems, utilizing various detection technologies, namely IMS, are quite complicated, climatic conditions-sensitive instruments, not very suitable for heavy-duty field and/or military application. Also, they require advanced level of operator's qualification and demanding training of the operator.

Systems and methods for reliable detection of various explosive traces are urgently needed and are now at the forefront of many research affords. The detection system should be extremely reliable, sensitive, the smallest sized, operating preferably only in vapor mode, resistant against cross-talking chemicals to avoid false alarms and very simple for operation without extensive training and special education of the operator. Under the standard environmental conditions, the detection of explosive traces is very complicated, especially, if we consider detection of all branch of non-volatile types of explosives. Moreover, interferences from various chemicals, human sweat, various solvents, and the like leads to false alarms, that are difficult to distinguish from actual positive detection.

The wide variety of techniques, used to sample explosives include manual swiping of the scanned subject in so called particulate mode or sampling the air, surrounding the scanned subject at ambient temperature and consequent pre-concentration to collect the most of the traces from the vicinity of the scanned subject. The manual swiping is not very popular, air sampling requires huge amount of air to be sampled and pre-concentrated to collect enough volume of traces to satisfy the system detection limit.

The variety of techniques, used to detect/analyze explosives, based on ion mobility spectrometry, IR spectroscopy, micro-wave spectroscopy, Raman or fluorescence spectrometry bring good detection limits, however all those principles feature low dynamic range and are very sensitive to cross-talks, caused by interfering chemicals, overloads and suffer from difficult cleaning if exposed by huge sampled concentration. Portable detection system built on above principles are usually complicated, big, heavy and not operationally robust enough to work reliably in the demanding field conditions, characterized by changing the humidity, temperature, dust and rough handling by the operator. High level of operator's training and adequate operator's education is obviously necessary for successful detection using above technologies, which limits the range of people usable to make the detection job.

Accordingly, there remains a need for a cost effective system to detect explosive traces with improved accuracy.

SUMMARY

In view of the foregoing, an embodiment herein provides an explosive detection system. The explosive detection system includes a detection unit, and a processing unit. The detection unit is configured to receive a desorbed sample. The detection unit includes a first heater, a second heater, a first resistance temperature detector (RTD), a second RTD, and an amplifier. The first heater is adapted to be exposed to the desorbed sample. The first heater and the second heater are adapted to be supplied with a specific voltage for three or more experiments. The first RTD is thermally coupled to the first heater. The second RTD is thermally coupled to the second heater. The first RTD and the second RTD are adapted to be supplied with constant current. The first RTD and the second RTD measure changes in resistance due to heating of the first heater and the second heater to calculate voltages across the first RTD and the second RTD. The amplifier is adapted to (i) amplify the voltages received from the first RTD and the second RTD to calculate a differential voltage for each of the three or more experiments, and (ii) convert the differential voltage into a digital signal. The processing unit is configured to process the digital signal to detect explosive trace in the desorbed sample. The processing unit includes a response processing module, a data processing module, a data normalization module, and an explosive detection module. The response processing module is configured to subtract the differential voltage of each of the three or more experiments with the differential voltage of the subsequent experiment to obtain a processed response. The data processing module is configured to (i) locate the position of minimum, and (ii) calculate summation of all values in the data set. The data normalization module is configured to calculate (a) a slope before the minimum value i.e. a first slope, and (b) a slope after the minimum value i.e. a second slope. The explosive detection module is configured to determine a presence of explosive trace in the desorbed sample when (i) the first slope is greater than a first cutoff slope, (ii) the second slope is greater than a second cutoff slope, and (iii) the data set summation is greater than a cutoff summation value.

In one embodiment, the data processing module is configured to (i) generate a graph for the processed responses, (ii) locate the position of minima, and (iii) calculate an area under the graph. The data normalization module is configured to calculate (a) a first slope, and (b) a second slope from the minima. The explosive detection module is configured to determine a presence of explosive trace in the desorbed sample when (i) the first slope is greater than a first cutoff slope, (ii) the second slope is greater than a second cutoff slope, and (iii) the area under the graph is greater than a cutoff area.

In another embodiment, the explosive detection system further includes one or more nanowires, and a heating element. The one or more nanowires are configured to collect a sample from one or more surfaces. The heating element is configured to heat the sample to a temperature ranging from 60° C. to 100° C. to obtain the desorbed sample. In yet another embodiment, the explosive detection system includes a display unit. The display unit is configured to display a status of one of (a) explosive trace is detected, or (b) no explosive trace is detected. In yet another embodiment, the processing unit determines (i) the specific voltage that is supplied to power the first heater and the second heater, and (ii) the constant current that is supplied to power the first RTD and the second RTD. In yet another embodiment, the first heater and the second heater are embedded with the first RTD and the second RTD respectively. In yet another embodiment, the first heater and the second heater are micro-heaters.

In another aspect, the explosive detector for detecting explosive in a vapor is provided. The explosive detector includes a detection unit, a processor unit and a display unit. The detection unit is configured to receive a desorbed vapor. The detection unit includes a first micro-heater, a second micro-heater, a first (resistance temperature detector) RTD, a second RTD, and an amplifier. The first micro-heater is adapted to be exposed to the desorbed vapor. The first micro-heater and the second micro-heater are adapted to be supplied with a specific voltage for the three or more experiments. The first RTD is embedded with the first micro-heater. The second RTD is embedded with the second micro-heater. The first RTD and the second RTD are adapted to be supplied with constant current. The first RTD and the second RTD measure changes in resistance due to heating of the first micro-heater and the second micro-heater to calculate voltages across the first RTD and the second RTD. The amplifier is adapted to (i) amplify the voltages received from the first RTD and the second RTD to calculate a differential voltage for each of the three or more experiments, and (ii) convert the differential voltage into a digital signal. The processing unit is configured to process the digital signal to detect explosive trace in the desorbed vapor. The processing unit includes a response processing module, a data processing module, a data normalization module, and an explosive detection module. The response processing module is configured to subtract the differential voltage of each of the three or more experiments with the differential voltage of the subsequent experiment to obtain a processed response. The data processing module is configured to (i) generate a graph for the processed responses, (ii) locate the position of minima, and (iii) calculate an area under the graph. The data normalization module is configured to calculate (a) a first slope, and (b) a second slope from the minima. The explosive detection module is configured to determine a presence of explosive trace in the desorbed vapor when (i) the first slope is greater than a first cutoff slope, (ii) the second slope is greater than a second cutoff slope, and (iii) the area under the graph is greater than a cutoff area. The display unit is configured to display a status of one of (a) explosive trace is detected, or (b) no explosive trace is detected. The processing unit determines (i) the specific voltage is supplied to power the first micro-heater and the second micro-heater, and (ii) the constant current is supplied to power the first RTD and the second RTD.

In one embodiment, the explosive detector includes one or more of nanowires, and a heating element. The one or more of nanowires are configured to collect a vapor from the one or more surfaces. The heating element that is configured to heat the vapor to a temperature ranging from 60° C. to 100° C. to obtain the desorbed vapor.

In yet another aspect, a method of detecting explosive trace in a sample is provided. The method includes the steps of: (i) receiving a sample into a detection unit for detecting explosive trace; and (ii) supplying a specific voltage to a first heater and a second heater for the one or more of experiments. The method further includes the steps of: (iii) measuring changes in resistance of the first RTD and the second RTD due to heating of the first heater and the second heater to calculate voltages across the first RTD and the second RTD; (iv) supplying a constant current to a first RTD and a second RTD; (v) measuring changes in resistance of the first RTD and the second RTD due to heating of the first heater and the second heater to calculate voltages across the first RTD and the second RTD; (vi) amplifying the voltages received from the first RTD and the second RTD to calculate a differential voltage for each of the one or more of experiments; (vii) converting the differential voltage into a digital signal; and (viii) processing the digital signal to detect explosive trace in the sample. The processing includes the steps of: (a) subtracting the differential voltage of each of the three or more experiments with the differential voltage of the subsequent experiment to obtain a processed response; (b) generating a graph for the processed responses; (c) locating the position of minima; (d) calculating an area under the graph; (e) calculating (i) a first slope, and (ii) a second slope from the minima; and (f) determining a presence of explosive trace in the sample when (i) the first slope is greater than a first cutoff slope, (ii) the second slope is greater than a second cutoff slope, and (iii) the area under the graph is greater than a cutoff area. In one embodiment, the method further includes a step of displaying a status of one of (a) explosive trace is detected, or (b) no explosive trace is detected.

The explosive detection system is highly selective, thereby reduces false positives/negatives while detecting explosives in a sample. The explosive detection system is highly sensitive in detecting explosives in a vapor and/or a particle phase. The explosive detection system is hand-held, and easily operable by a user/security personnel. The explosive detection system is easy to maintain. The explosive detection system may be supplied with battery power, thereby reduces the power consumption. The explosive detection system detects a very broad range of explosives materials/traces. The first RTD and the second RTD may be linear in shape. The first RTD and the second RTD is highly accurate in measuring temperature by correlating the resistance of the RTD element with temperature. The first RTD and the second RTD may be easily fabricated with any device using simpler micro-fabrication processes. The explosive detection system may be deployed in public transport carriers like buses, trains, etc. and connected to a centralized monitoring/computing device (e.g., a tablet, a phone, etc.) using standard wireless protocols for transmission of results/data.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

Figure 1A:
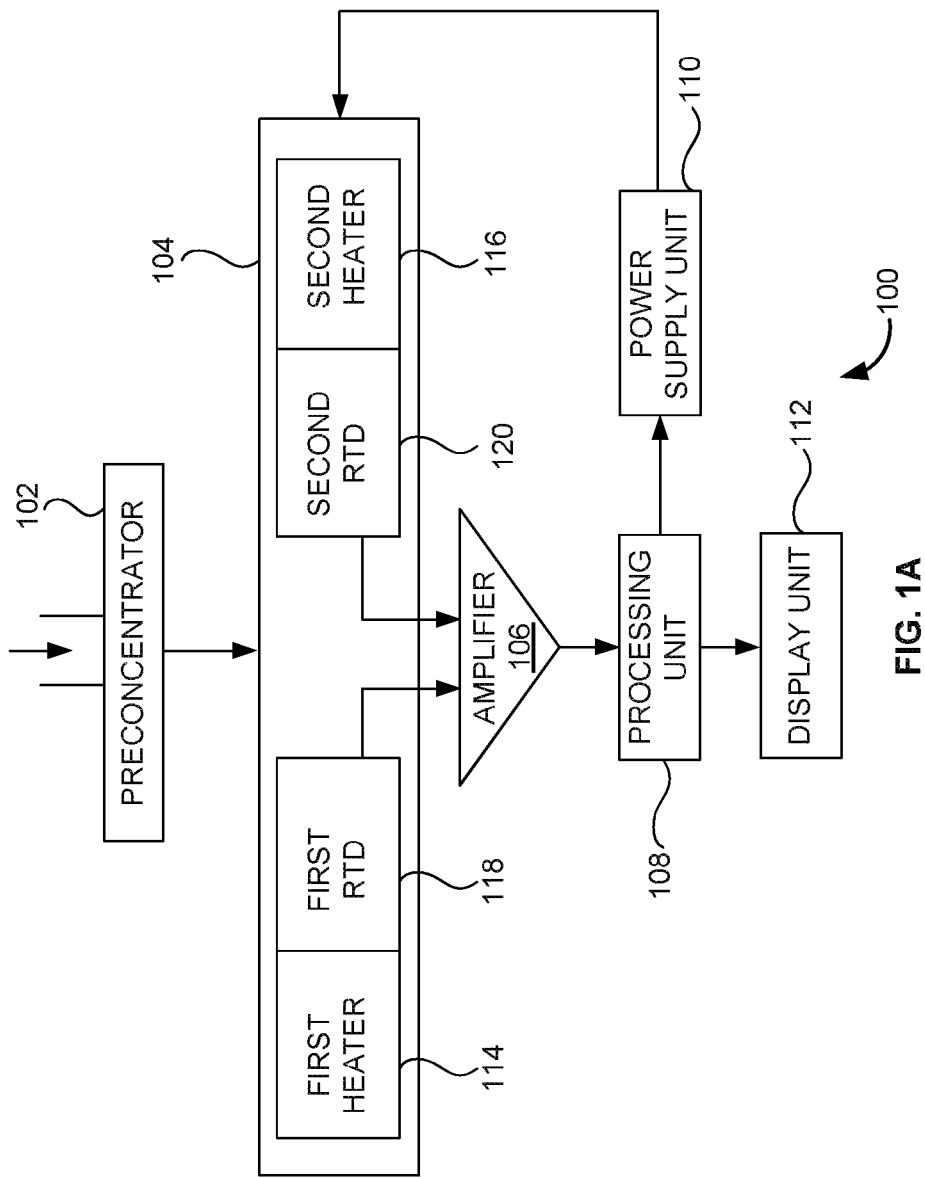
FIG. 1A illustrates a block diagram of an explosive detection system according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Various embodiments of the methods and systems disclosed herein provide an explosive detection system that includes a pre-concentrator, a detection unit, and a processing unit. The pre-concentrator provides larger surface area to collect samples (e.g., vapors, particles, etc.) The pre-concentrator includes one or more nanowires and a heating element. The one or more nanowires collect samples from one or more surfaces. The heating element heats the samples to a temperature of about 60° C.-100° C. to obtain desorbed sample. The detection unit receives the desorbed sample for detection of explosive traces. The detection unit includes two micro-heaters embedded with RTD's (Resistance Temperature Detector). One of the micro-heaters is exposed to the desorbed vapor/analyte, and the other micro-heater is used as reference. The detection unit measures voltages across two RTDs to calculate a differential voltage. The detection unit further converts the differential voltage/signal into a digital signal, and transmits the digital signal to the processing unit for further processing. The processing unit processes the digital signal to detect explosive trace in the desorbed sample. Referring now to the drawings, and more particularly to FIGS. 1 through 7, where similar reference characters denote corresponding features consistently throughout the figures, there are shown preferred embodiments.

FIG. 1A illustrates a block diagram of an explosive detection system 100 according to an embodiment herein. The explosive detection system 100 includes a pre-concentrator 102, a detection unit 104, an amplifier 106, a processing unit 108, a power supply unit 110, and a display unit 112. The pre-concentrator 102 includes one or more nanowires, and a heating element. The one or more nanowires collect samples (e.g., vapors, particles, etc.) from one or more surfaces. The heating element heats the samples/vapors to a temperature ranging from 60° C. to 100° C. to obtain desorbed sample. In one embodiment, the pre-concentrator 102 includes a sampling unit to collect the samples. The desorbed sample is drawn into the detection unit for detection of explosive traces. In one embodiment, the detection unit includes a receiving unit that receives the desorbed sample. In another embodiment, the desorbed sample/vapor is drawn into the detection unit by at least one of (a) plain suction using a pump/suction pump, and (b) swiping the sample. After swiping the sample, the swiped sample is drawn into the detection unit 104 by (a) blowing hot air through the swiped sample, or (b) heating and suctioning the swiped sample. The detection unit 104 includes a first heater 114, a second heater 116, a first RTD (Resistance Temperature Detector) 118, and a second RTD 120. In one embodiment, the first heater 114, and the second heater 116 are micro-heaters. The first heater 114 is coupled with the first RTD 118. The second heater 116 is coupled with the second RTD 120. In one embodiment, the first heater 114 is embedded with the first RTD 118. In another embodiment, the second heater 116 is embedded with the second RTD 120. The first heater 114 and the second heater 116 are adapted to be supplied with a specific voltage for three or more experiments using the power supply unit 110. The first RTD 118 and the second RTD 120 are adapted to be supplied with constant current using the power supply unit 110. In one embodiment, the processing unit 108 determines (a) a specific voltage that is supplied to power the first heater 114 and the second heater 116, and (b) a constant current that is supplied to power the first RTD 118 and the second RTD 120. The first heater 114 that is adapted to be exposed to the desorbed sample (i.e. analyte). The second heater 116 is used as a reference heater. When the specific voltage is applied to the first heater 114 and the second heater 116, the temperature of the first heater 114, and the second heater 116 rises to a temperature ranging from 300° C. to 500° C., and falls back to a room temperature. The first heater that is exposed to the desorbed sample 114 imparts a different temperature signature due to (a) melting, (b) sublimation, and (c) evaporation of the desorbed sample/vapor, compare to the second heater 116. This in turn, results in change in resistance of the first RTD 118 and the second RTD 120. In one embodiment, when (a) the first heater 114 is exposed to the desorbed sample, and (b) a specific voltage is applied to the first heater 114, the desorbed sample that includes explosive is deflagrated, leading to a different temperature signature. The first RTD 118 and the second RTD 120 measure changes in resistance due to heating of the first heater 114 and the second heater 116 to calculate voltages across the first RTD 118 and the second RTD 120. The detection unit 104 further includes an amplifier to amplify the voltages received from the first RTD 118 and the second RTD 120 to calculate a differential voltage for each of the three or more experiments. In one embodiment, the detection unit 104 measures voltages across the first RTD 118, and the second RTD 120 based on differential thermal analysis, or differential scanning calorimetry. The amplifier further converts the differential voltage into a digital signal, and transmits the digital signal to the processing unit for further processing.

The processing unit 108 processes the digital signal to detect explosive traces in the desorbed sample/vapor. In one embodiment, the processing unit 108 selectively remove non-explosive samples/vapors based on different pulse width, pulse pitch, pulse magnitude of heating profiles. The display unit 112 displays a status that is selected from one of (a) explosive trace is detected, or (b) no explosive trace is detected. In one embodiment, the display unit 112 provides a LED notification. When a red LED glows in the display unit 112, the explosive trace is detected in the desorbed sample. When an orange LED glows in the display unit 112, the vapor/sample (i.e. desorbed sample) needs to be tested again. When a green LED glows in the display unit 112, the explosive trace is not detected in the desorbed sample. In another embodiment, the display unit 112 displays a notification as text according to LED notification.

Figure 1B:
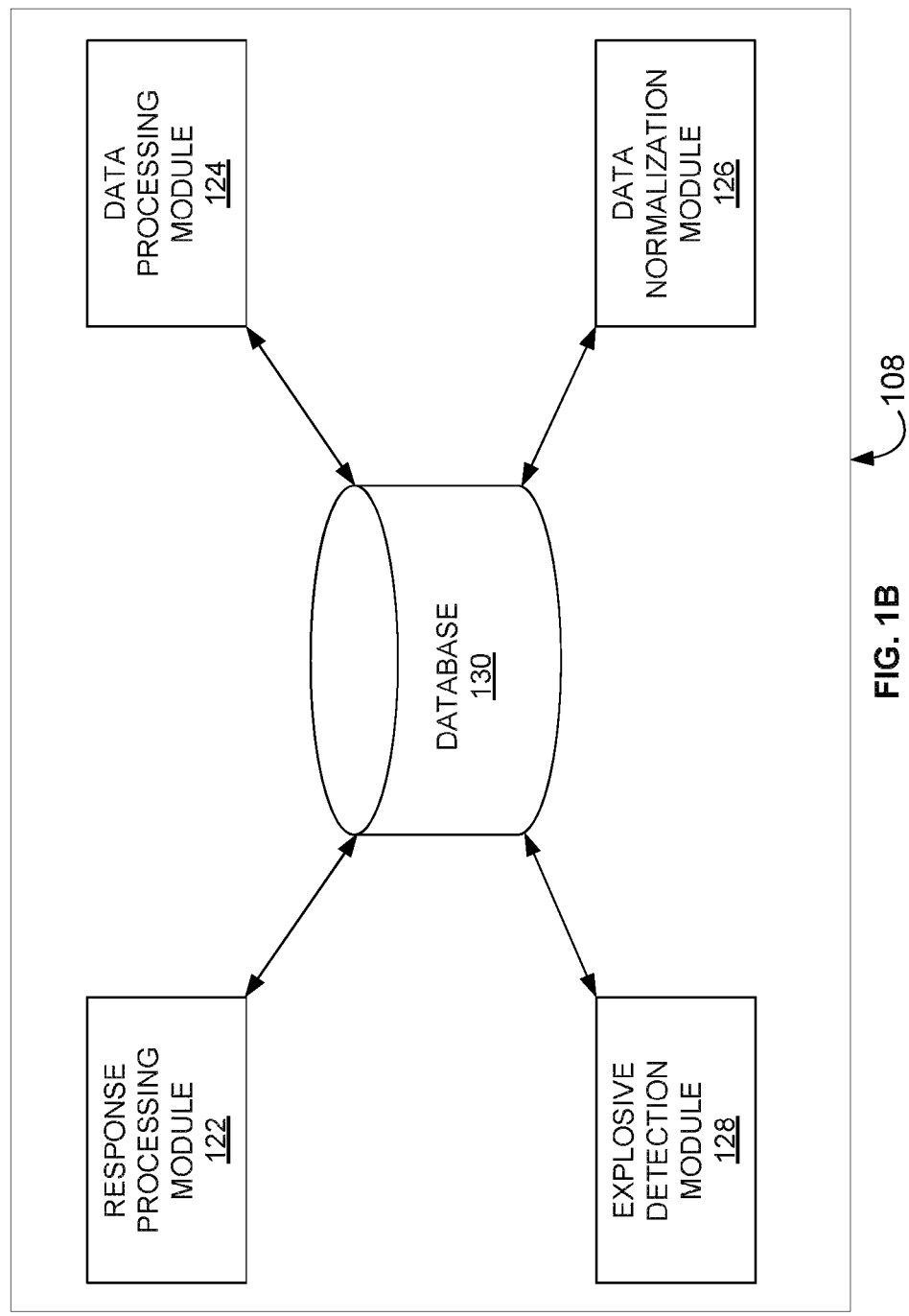
FIG. 1B illustrates an exploded view of the processing unit of FIG. 1 according to an embodiment herein.

With reference to FIG. 1A, FIG. 1B illustrates an exploded view of the processing unit 108 according to an embodiment herein. The processing unit process the digital signal received from the detection unit 104 to detect explosive trace in the desorbed sample. The processing unit 108 includes a response processing module 122, a data processing module 124, a data normalization module 126, an explosive detection module 128 and a database 130. The response processing module 122 is configured to subtract the differential voltage of each of the three or more experiments with the differential voltage of the subsequent experiment to obtain a processed response. The data processing module 124 is configured to (i) generate a graph for the processed responses, (ii) locate the position of minima, and (iii) calculate an area under the graph. The data normalization module 126 is configured to calculate (a) a first slope, and (b) a second slope from the minima. The explosive detection module 128 is configured to determine a presence of explosive trace in the desorbed sample when (i) the first slope is greater than a first cutoff slope, (ii) the second slope is greater than a second cutoff slope, and (iii) the area under the graph is greater than a cutoff area.

In one embodiment, the data processing module 124 is configured to (i) locate the position of minimum, and (ii) calculate summation of all values in the data set. The data normalization module 126 calculates (a) a slope before the minimum value i.e. a first slope, and (b) a slope after the minimum value i.e. a second slope. The explosive detection module 128 determines a presence of explosive trace in the desorbed sample when (i) the first slope is greater than a first cutoff slope, (ii) the second slope is greater than a second cutoff slope, and (iii) the data set summation is greater than a cutoff summation value.

In another embodiment, when an explosive is detected in a sample, the explosive goes through the phases of absorption, melting, evaporation, and/or decomposition. The slopes of a processed response to the input pulse (e.g., 20 ms of a specific voltage) for each of the three or more experiments are analyzed electronically as follows: (i) a dip in the processed response that indicates absorption of energy, and presence of substantial thermal mass in the form of explosive, (ii) a lowest point of the dip, and (iii) a sudden rise of processed response that indicates the evaporation of the vapors generated, and the subsequent release of heat. The lowest point of the dip in the processed response of the first heater 114 indicates a state of the explosives changes thereby generating large amount of vapor.

Figure 2:
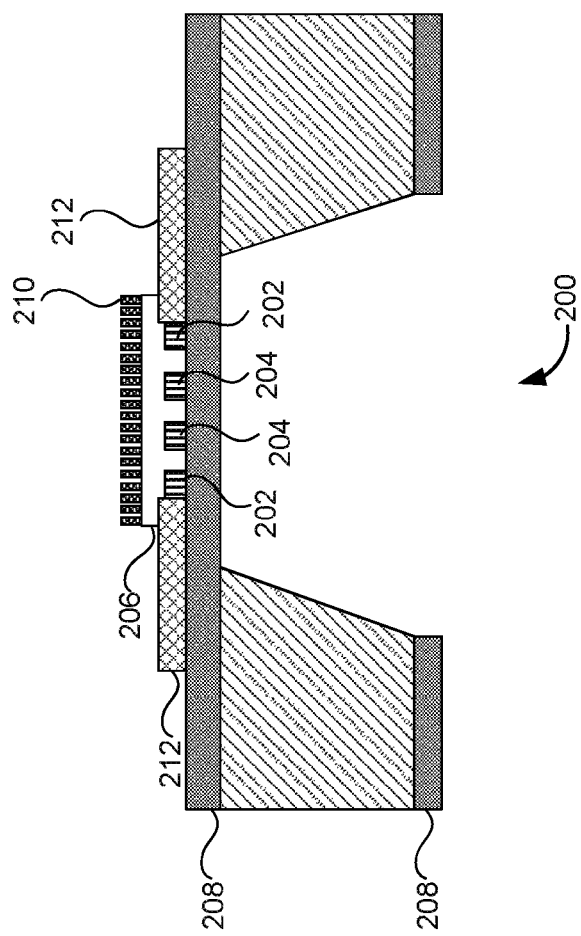
FIG. 2 illustrates a system view of the heaters of FIG. 1 according to an embodiment herein.

FIG. 2 illustrates a system view 200 of the heaters of FIG. 1 according to an embodiment herein. The heater (e.g., the first heater 114, or the second heater 116) includes one or more heater coils 202, one or more RTD coils 204, a silicon nitride membrane 206, a silicon dioxide membrane 208, the one or more nanowires 210, and one or more contact pads 212. The one or more heater coil 202, and the one or more RTD coils 204 are sandwiched in between the silicon nitride membrane 206, and the silicon dioxide membrane 208. The one or more nanowires 210 are coupled to the silicon nitride membrane 206. In one embodiment, the one or more nanowires 210 are attached to the silicon nitride membrane 206 using a hydro-thermal process. In another embodiment, the one or more nanowires 210 provides an increased surface area to collect samples/vapors, and adsorb moisture of the samples/vapors. The heater (e.g., the first heater 114, or the second heater 116) generates heat inside the detection unit 104 upon providing a specific electrical voltage by the power supply unit 110. In one embodiment, the heater (e.g., the first heater 114, or the second heater 116) is subjected to rapid temperature changes due to thermal inertia/heating. This in turn, results in change in resistance of the first RTD 118 and the second RTD 120. The one or more contact pads 212 provide electrical contact for the heaters. In one embodiment, the one or more contact pads 212 are gold pads. In another embodiment, a thickness of the silicon dioxide membrane 208 is 800 nm (nanometer). In yet another embodiment, a thickness of the silicon nitride membrane 206 is 120 nm. In yet another embodiment, a resistance of (i) the one or more heater coils 202 at 25° C. is 160-200Ω, and (ii) the one or more RTD coils 204 at 25° C. is 120-160Ω. In yet another embodiment, a thickness of the one or more heater coils 202 is 180 nm. In yet another embodiment, a width of the one or more heater coils 202 is 10 μm. In yet another embodiment, a length of the one or more heater coils 202 is 1.2 mm. In yet another embodiment, a size of the heating area of the one or more heater coils 202 is 500 μm×500 μm. The one or more heater coils 202 is made up of platinum. In one embodiment, the one or more heater coils 202 is made up of aluminum, poly silicon, or nichrome.

Figure 3:
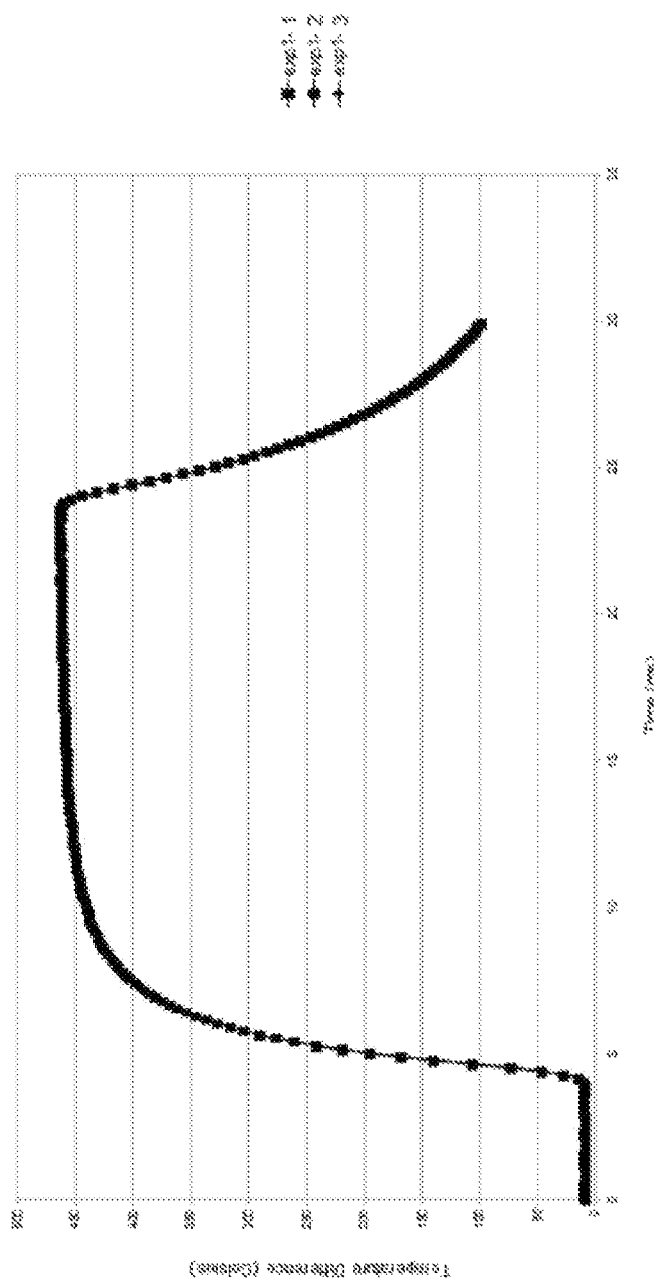
FIG. 3 is a graphical representation that illustrates responses of the heaters of FIG. 1 to an input pulse according to an embodiment herein.

FIG. 3 is a graphical representation that illustrates responses of the heaters of FIG. 1 to an input pulse according to an embodiment herein. The graphical representation includes a X-axis and a Y-axis. The X-axis is plotted with time in milliseconds, and the Y-axis is plotted with temperature in ° C. The responses of the first heater 114, and the second heaters 116 are measured in response to the input pulse (e.g., 20 ms of a specific voltage) for the three or more experiments. The responses of the first heater 114 (i.e. voltage) are measured against a baseline, to obtain a differential voltage. The baseline is the average responses of the second heater 116 to the input pulse for the three or more experiments (e.g., 10 experiments).

Figure 4A:
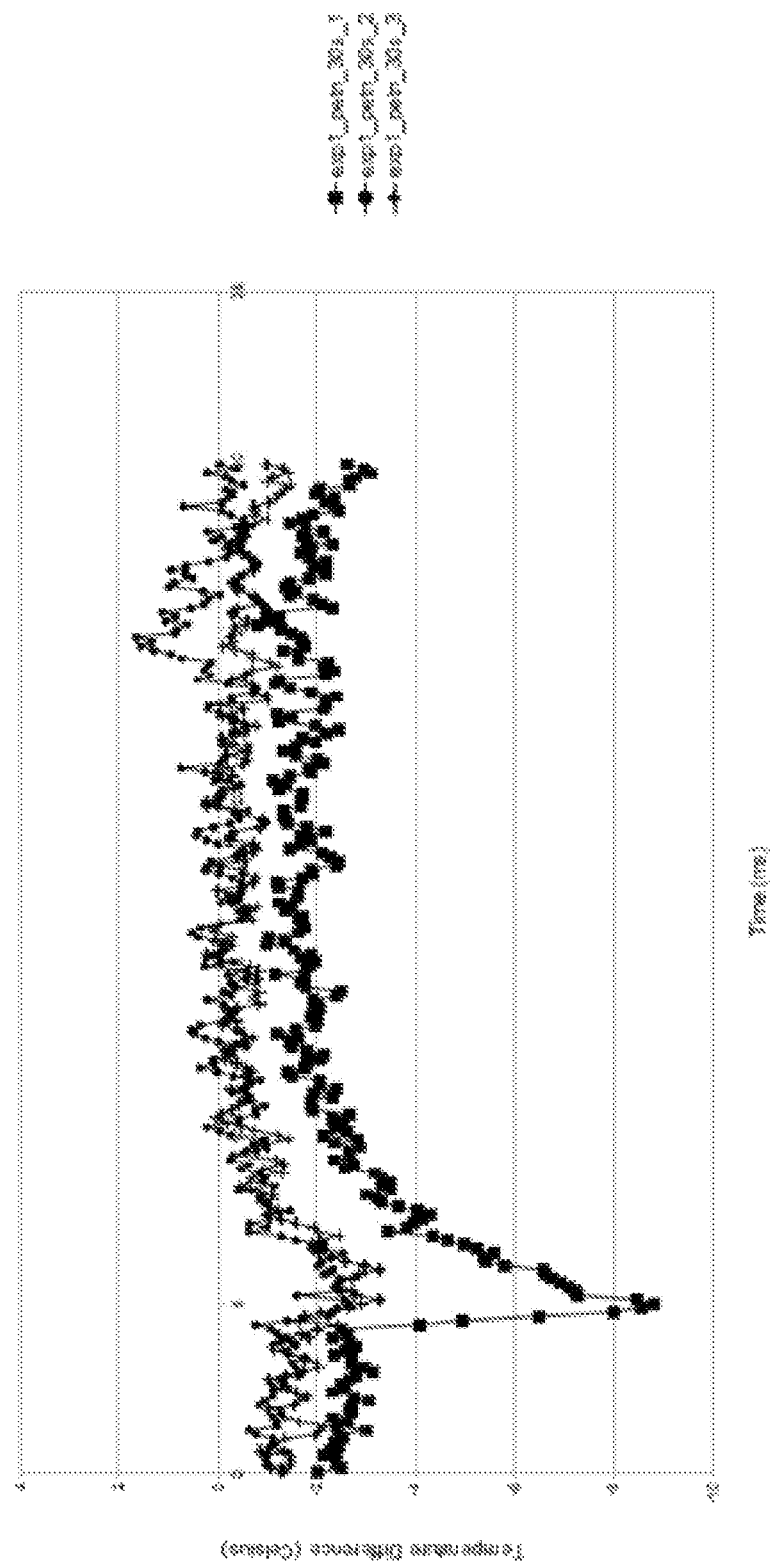
FIG. 4A is a graphical representation that illustrates processed responses of the explosive detection system of FIG. 1 to a sample that includes a pentaerythritol tetranitrate explosive according to an embodiment herein.

FIG. 4A is a graphical representation illustrates processed responses of the explosive detection system 100 of FIG. 1 to a sample that includes a pentaerythritol tetranitrate explosive according to an embodiment herein. The graphical representation includes an X-axis and a Y-axis. The X-axis is plotted with time in milliseconds, and the Y-axis is plotted with temperature in ° C. The responses of the first heater 114, which is exposed to a sample containing pentaerythritol tetranitrate explosive, are measured in response to the input pulse (e.g., 20 ms of a specific voltage) for the three or more experiments. The response of the first heater 114 is measured against a baseline to obtain a differential voltage. When the sample/vapor includes pentaerythritol tetranitrate explosive, the differential voltage for the input pulse for a first experiment is found to be distinctively different from the differential voltages for the remaining experiments. The differential voltage obtained from the first experiment and the differential voltage obtained from the subsequent experiment is processed to obtain a processed response. The slopes of the processed response are analyzed to detect the pentaerythritol tetranitrate explosive in the sample.

Figure 4B:
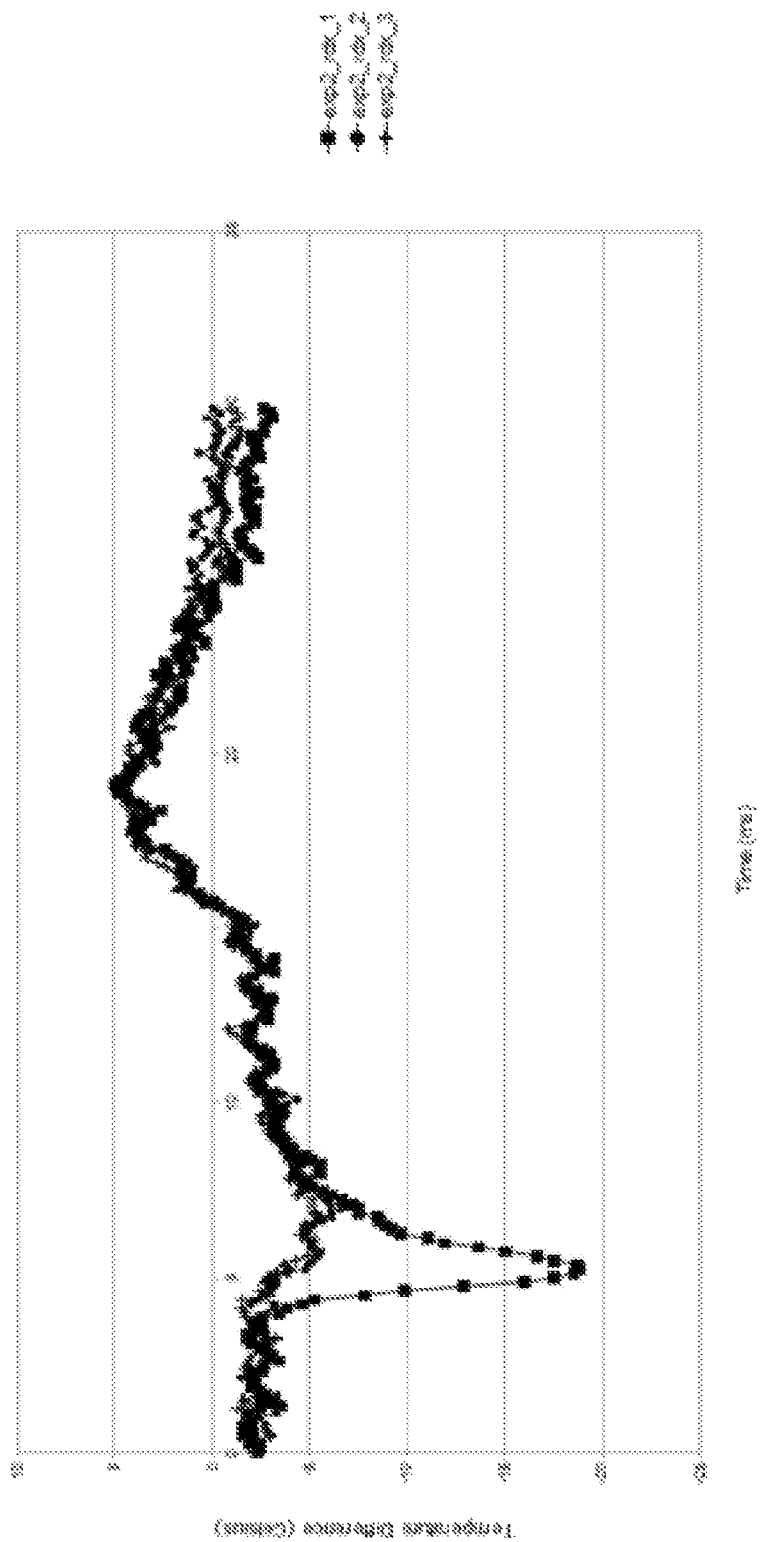
FIG. 4B illustrates is a graphical representation that illustrates processed responses of the explosive detection system of FIG. 1 to a sample that includes a RDX explosive according to an embodiment herein.

FIG. 4B illustrates is a graphical representation illustrates processed responses of the explosive detection system 100 of FIG. 1 to a sample that includes a research department explosive (RDX) according to an embodiment herein. The graphical representation includes a-X axis and a-Y axis. The X-axis is plotted with time in milliseconds, and the Y-axis is plotted with temperature in ° C. The responses of the first heater 114, which is exposed to a sample containing a RDX explosive, are measured in response to the input pulse (e.g., 20 ms of a specific voltage) for the three or more experiments. The response of the first heater 114 is measured against a baseline to obtain a differential voltage. When the sample/vapor includes RDX explosive, the differential voltage for the input pulse for the first experiment is found to be distinctively different from the differential voltages for the remaining experiments. The differential voltage obtained from the first experiment and the differential voltage obtained from the subsequent experiment is processed to obtain a processed response. The slopes of the processed response are analyzed to detect the RDX explosive in the sample.

Figure 4C:
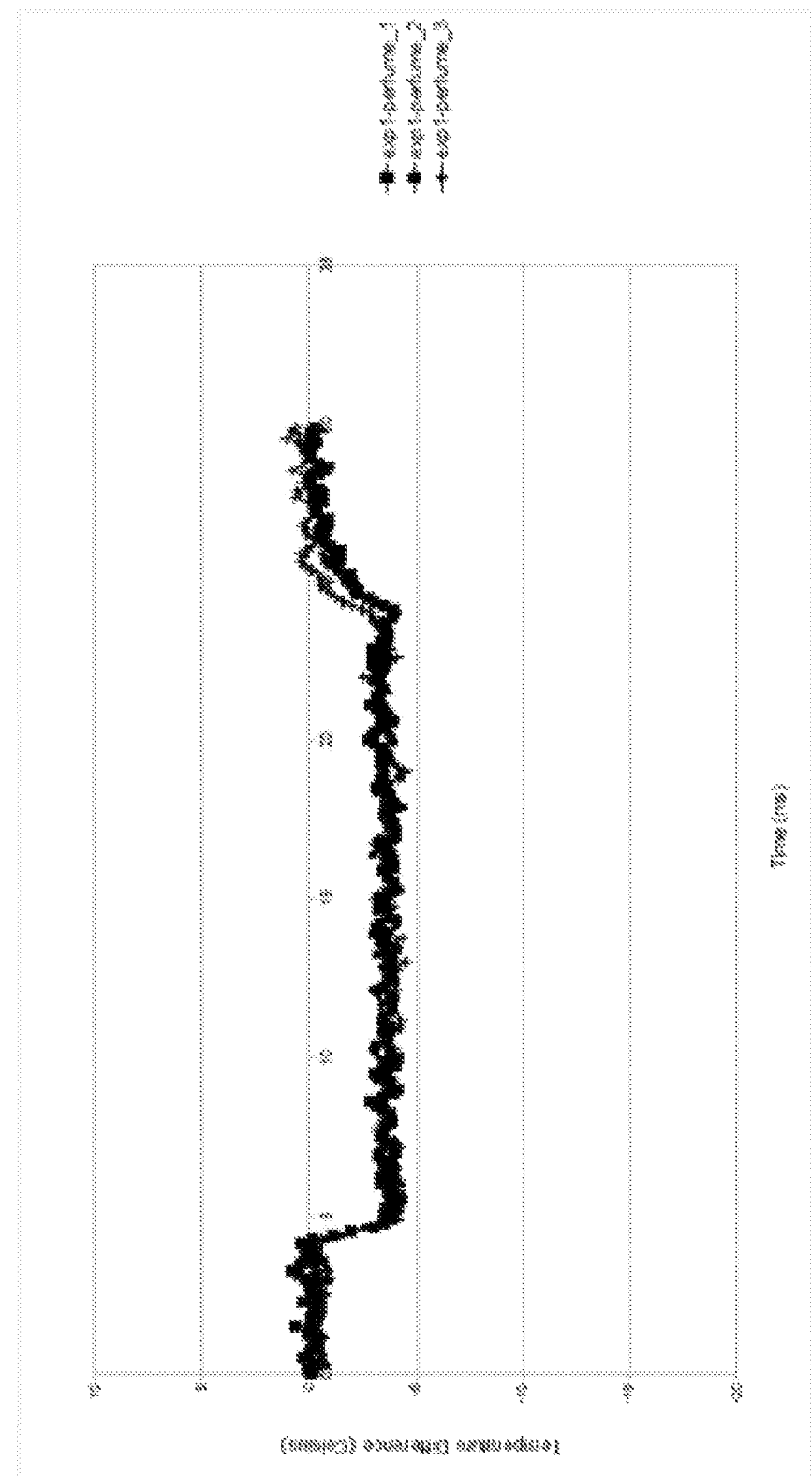
FIG. 4C is a graphical representation illustrates processed responses of the explosive detection system of FIG. 1 to a sample that includes no explosive traces according to an embodiment herein.

FIG. 4C is a graphical representation illustrates processed responses of the explosive detection system 100 of FIG. 1 to a sample that includes no explosive traces (i.e. includes perfumes) according to an embodiment herein. The graphical representation includes an X-axis and a Y-axis. The X-axis is plotted with time in milliseconds, and the Y-axis is plotted with temperature in ° C. The response of the first heater 114 is measured against a baseline, to obtain a differential voltage. In one embodiment, the baseline is the average responses of the second heater 116 (i.e. non-exposed heater) to an input pulse for the three or more experiments.

Figure 5A:
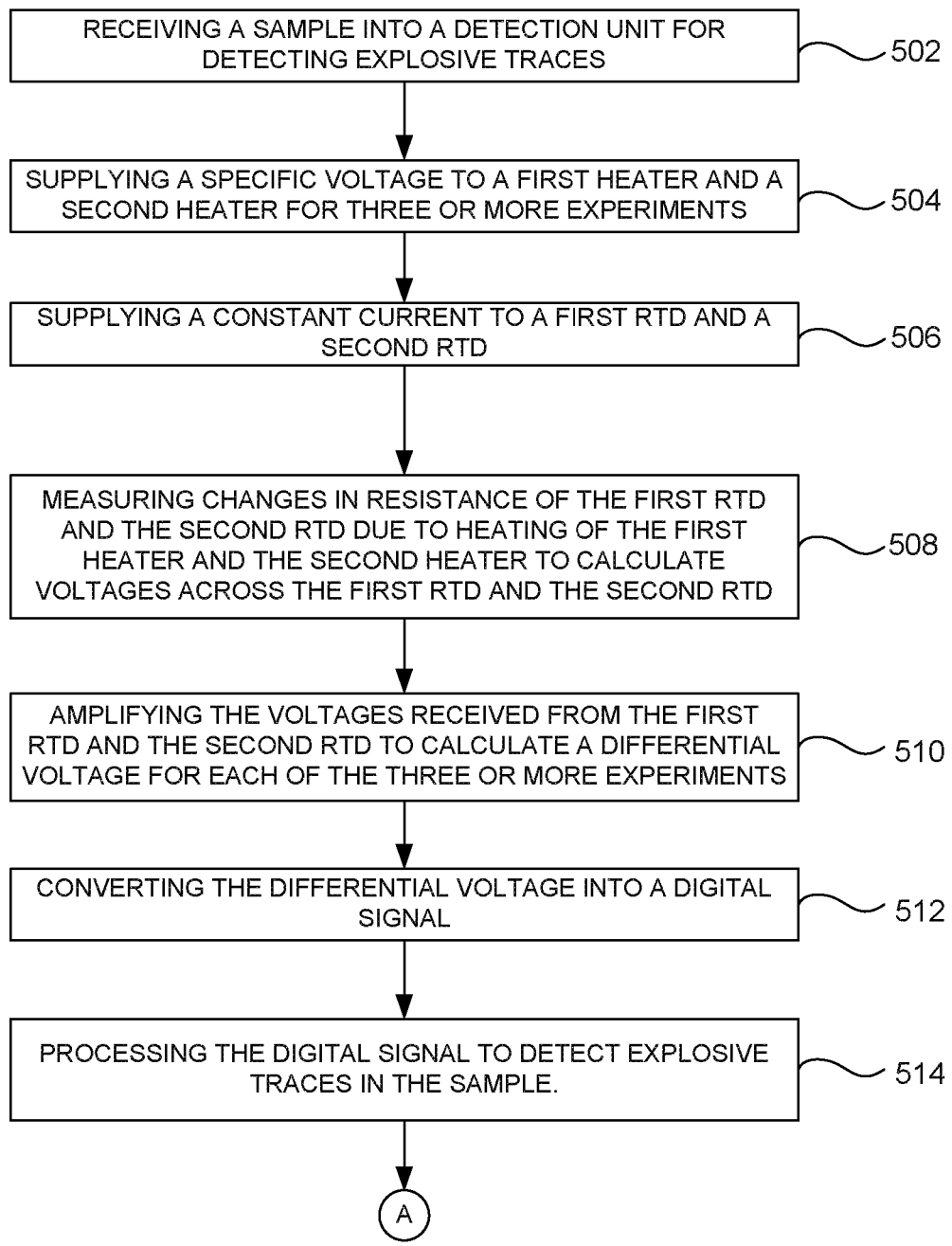
FIG. 5A and FIG. 5B are flow diagrams illustrating a method of detecting an explosive using the explosive detection system of FIG. 1 according to an embodiment herein.
Figure 5B:
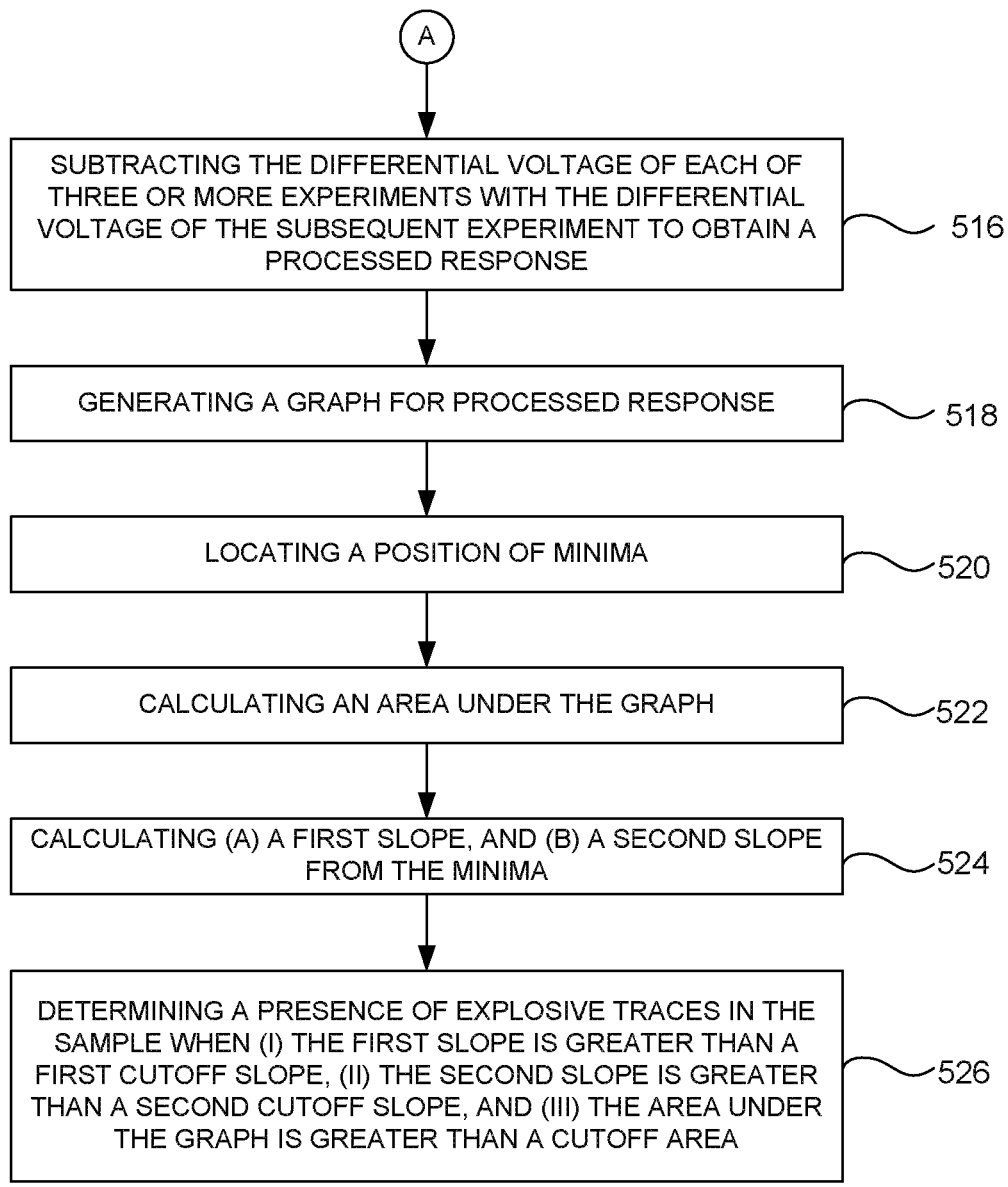

FIG. 5A and FIG. 5B are flow diagrams illustrating a method of detecting an explosive using the explosive detection system of FIG. 1 according to an embodiment herein. At step 502, the desorbed sample is drawn into the detection unit for detection of explosive traces. In one embodiment, the detection unit includes a receiving unit that receives the desorbed sample. At step 504, the first heater 114 and the second heater 116 are adapted to be supplied with a specific voltage for three or more experiments using the power supply unit 110. At step 506, the first RTD 118 and the second RTD 120 are adapted to be supplied with constant current using the power supply unit 110. At step 508, the first RTD 118 and the second RTD 120 measure changes in resistance due to heating of the first heater 114 and the second heater 116 to calculate voltages across the first RTD 118 and the second RTD 120. At step 510, the detection unit 104 includes an amplifier to amplify the voltages received from the first RTD 118 and the second RTD 120 to calculate a differential voltage for each of the three or more experiments. In one embodiment, the detection unit 104 measures voltages across the first RTD 118, and the second RTD 120 based on differential thermal analysis, or differential scanning calorimetry. At step 512, the amplifier further converts the differential voltage into a digital signal, and transmits the digital signal to the processing unit for further processing. At step 514, the processing unit 108 processes the digital signal to detect explosive traces in the desorbed sample/vapor. In one embodiment, the processing unit 108 selectively remove non-explosive samples/vapors based on different pulse width, pulse pitch, pulse magnitude of heating profiles. At step 516, the response processing module 122 is configured to subtract the differential voltage of each of the three or more experiments with the differential voltage of the subsequent experiment to obtain a processed response. At step 518, the data processing module 124 is configured to generate a graph for the processed responses. At step 520, the data processing module 124 is configured to locate the position of minima. At step 522, the data processing module 124 is configured to calculate an area under the graph. At step 524, the data normalization module 126 is configured to calculate (a) a first slope, and (b) a second slope from the minima. At step 526, the explosive detection module 128 is configured to determine a presence of explosive trace in the desorbed sample when (i) the first slope is greater than a first cutoff slope, (ii) the second slope is greater than a second cutoff slope, and (iii) the area under the graph is greater than a cutoff area.

In one embodiment, the data processing module 124 is configured to (i) locate the position of minimum, and (ii) calculate summation of all values in the data set. The data normalization module 126 calculates (a) a slope before the minimum value i.e. a first slope, and (b) a slope after the minimum value i.e. a second slope. The explosive detection module 128 determines a presence of explosive trace in the desorbed sample when (i) the first slope is greater than a first cutoff slope, (ii) the second slope is greater than a second cutoff slope, and (iii) the data set summation is greater than a cutoff summation value.

In another embodiment, the pre-concentrator 102 includes one or more nanowires, and a heating element. The one or more nanowires collect samples (e.g., vapors, particles, etc.) from one or more surfaces. In yet another embodiment, the pre-concentrator 102 includes a sampling unit to collect the samples.

Figure 6:
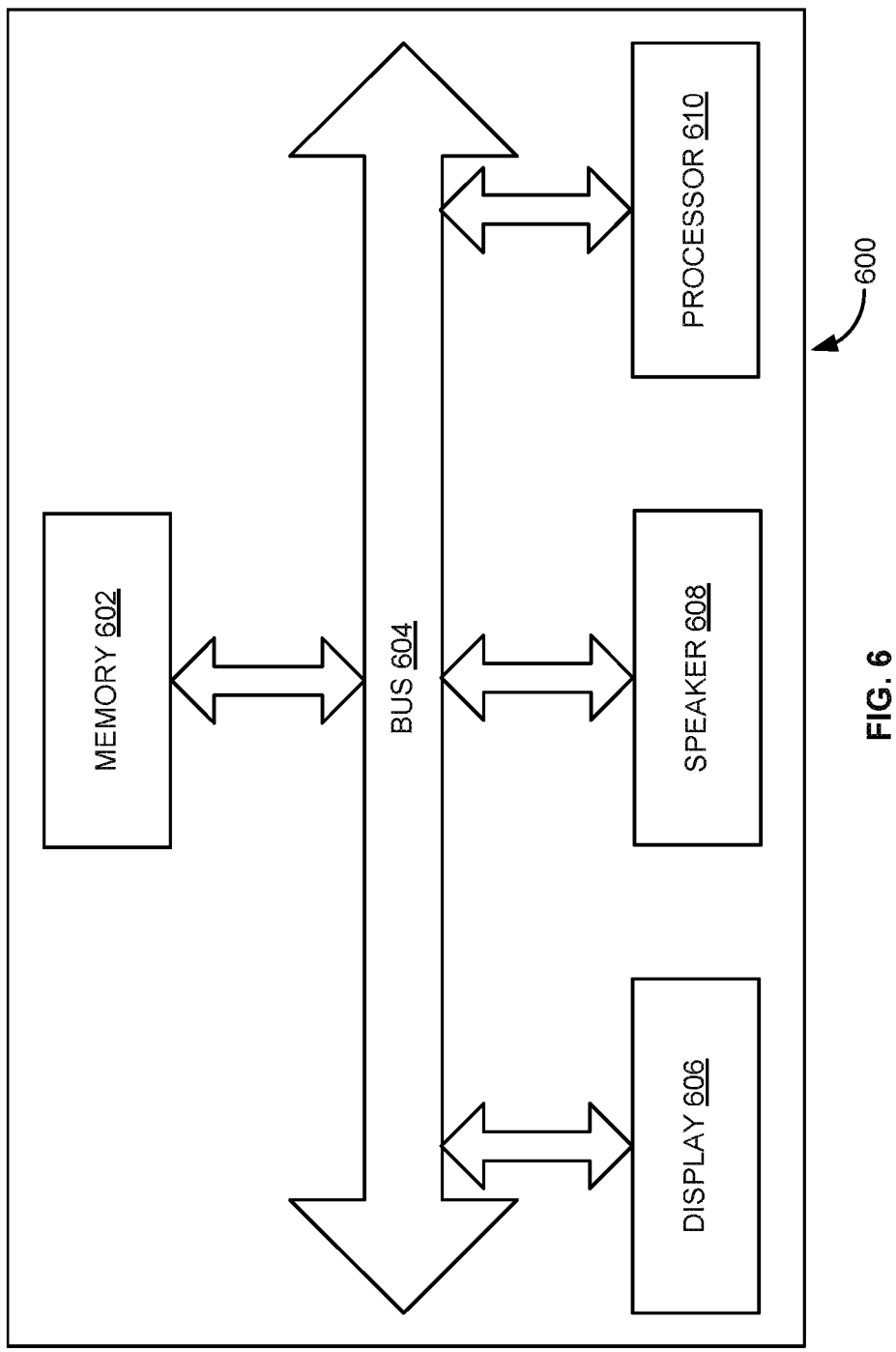
FIG. 6 illustrates an exploded view of the receiver of FIG. 1 according to an embodiment herein.

FIG. 6 illustrates an exploded view of the receiver 600 of FIG. 1 having an a memory 602 having a set of instructions, a bus 604, a display 606, a speaker 608, and a processor 610 capable of processing the set of instructions to perform any one or more of the methodologies herein, according to an embodiment herein. The processor 610 may also enable digital content to be consumed in the form of video for output via one or more displays 606 or audio for output via speaker and/or earphones 608. The processor 610 may also carry out the methods described herein and in accordance with the embodiments herein.

Digital content may also be stored in the memory 602 for future processing or consumption. The memory 602 may also store program specific information and/or service information (PSI/SI), including information about digital content (e.g., the detected information bits) available in the future or stored from the past. A user of the receiver 600 may view this stored information on display 606 and select an item of for viewing, listening, or other uses via input, which may take the form of keypad, scroll, or other input device(s) or combinations thereof. When digital content is selected, the processor 610 may pass information. The content and PSI/SI may be passed among functions within the receiver using the bus 604.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly.

The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The embodiments herein can take the form of, an entirely hardware embodiment, an entirely software embodiment or an embodiment including both hardware and software elements. The embodiments that are implemented in software include but are not limited to, firmware, resident software, microcode, etc. Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, remote controls, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 7:
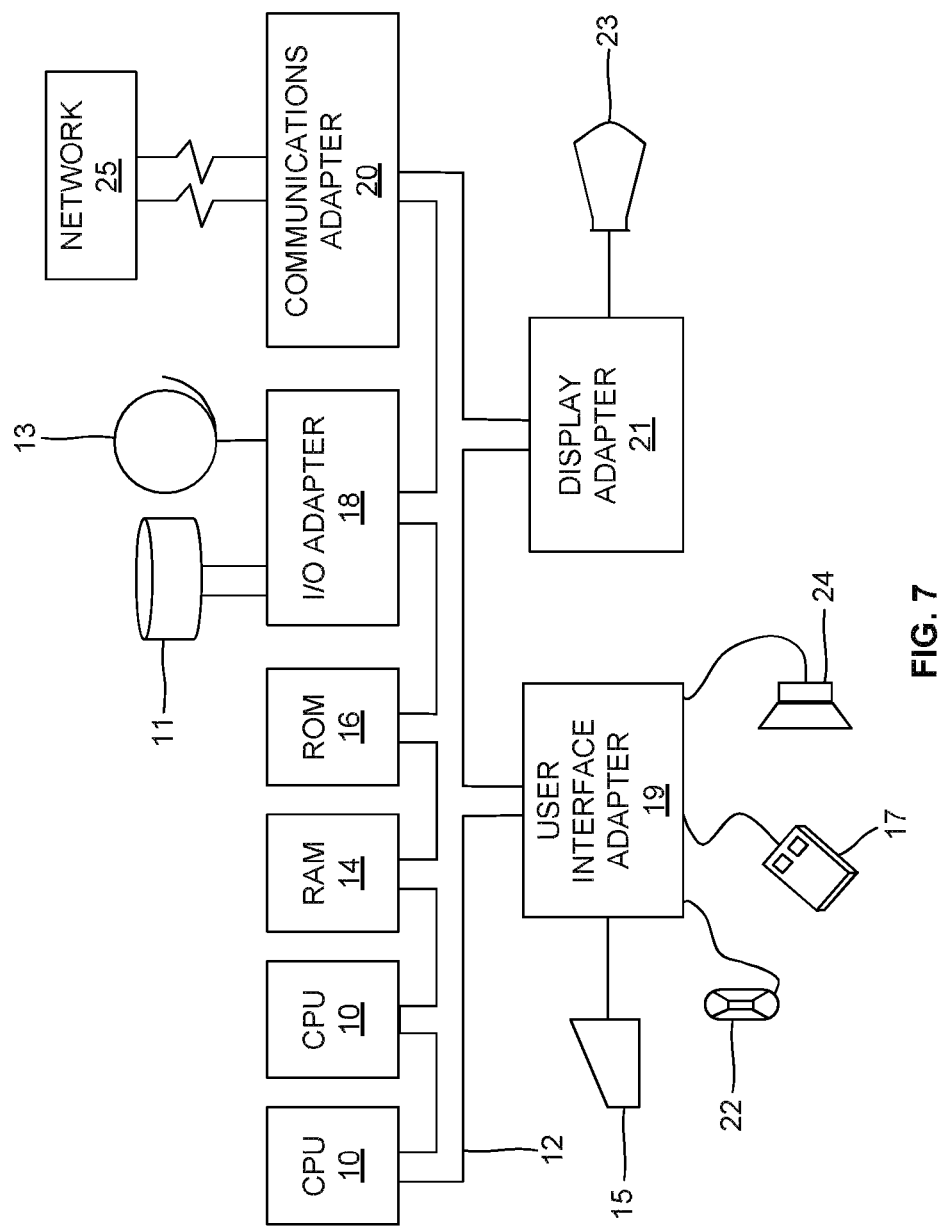
FIG. 7 illustrates a schematic diagram of a computer architecture used according to an embodiment herein.

A representative hardware environment for practicing the embodiments herein is depicted in FIG. 7. This schematic drawing illustrates a hardware configuration of a computer architecture/computer system in accordance with the embodiments herein. The system comprises at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of the embodiments herein.

The system further includes a user interface adapter 19 that connects a keyboard 15, mouse 17, speaker 24, microphone 22, and/or other user interface devices such as a touch screen device (not shown) or a remote control to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An explosive detection system comprising:
   a detection unit that is configured to receive a desorbed sample, wherein said detection unit comprises:
      a first heater that is adapted to be exposed to the desorbed sample;
      a second heater, wherein the first heater and the second heater are adapted to be supplied with a specific voltage for a plurality of experiments;
      a first resistance temperature detector (RTD) that is thermally coupled to the first heater;
      a second RTD that is thermally coupled to the second heater, wherein the first RTD and the second RTD are adapted to be supplied with constant current, wherein the first RTD and the second RTD measure changes in resistance due to heating of the first heater and the second heater to calculate voltages across the first RTD and the second RTD; and
      an amplifier that is adapted to (i) amplify the voltages received from the first RTD and the second RTD to calculate a differential voltage for each of the plurality of experiments, and (ii) convert the differential voltage into a digital signal; and
   a processing unit that is configured to process the digital signal to detect explosive trace in the desorbed sample, wherein said processing unit comprises:
      a response processing module that is configured to subtract the differential voltage of each of the three or more experiments with the differential voltage of the subsequent experiment to obtain a processed response;
      a data processing module that is configured to (i) locate a position of minimum value, and (ii) calculate summation of all values in dataset;
      a data normalization module that is configured to calculate (a) a first slope before the minimum value, and (b) a second slope after the minimum value; and
      an explosive detection module that is configured to determine a presence of explosive trace in the desorbed sample when (i) the first slope is greater than a first threshold slope, (ii) the second slope is greater than a second threshold slope, and (iii) the data set summation is greater than a threshold summation value.

2. The system of claim 1, wherein the system comprises:
   a plurality of nanowires that is configured to collect a sample from a plurality of surfaces; and
   a heating element that is configured to heat the sample to a temperature ranging from 60° C. to 100° C. to obtain the desorbed sample.

3. The system of claim 1, wherein the system comprises a display unit that is configured to display a status of one of (a) explosive trace is detected, or (b) no explosive trace is detected.

4. The system of claim 1, wherein the processing unit determines (i) the specific voltage that is supplied to power the first heater and the second heater, and (ii) the constant current that is supplied to power the first RTD and the second RTD.

5. The system of claim 1, wherein the first heater and the second heater are embedded with the first RTD and the second RTD respectively.

6. The system of claim 1, wherein the processing unit comprises:
   the data processing module that is configured to (i) generate a graph for the processed responses, (ii) locate the position of minima, and (iii) calculate an area under the graph;
   the data normalization module that is configured to calculate (a) a first slope, and (b) a second slope from the minima; and
   the explosive detection module that is configured to determine a presence of explosive trace in the desorbed vapor when (i) the first slope is greater than a first threshold slope, (ii) the second slope is greater than a second threshold slope, and (iii) the area under the graph is greater than a threshold area.

7. An explosive detector comprising:
   a detection unit that is configured to receive a desorbed vapor, said detection unit comprising:
      a first micro-heater that is adapted to be exposed to the desorbed vapor;
      a second micro-heater, wherein the first micro-heater and the second micro-heater are adapted to be supplied with a specific voltage for a plurality of experiments;
      a first resistance temperature detector (RTD) that is embedded with the first micro-heater;
      a second RTD that is embedded with the second micro-heater, wherein the first RTD and the second RTD are adapted to be supplied with constant current, wherein the first RTD and the second RTD measure changes in resistance due to heating of the first micro-heater and the second micro-heater to calculate voltages across the first RTD and the second RTD; and
      an amplifier that is adapted to (i) amplify the voltages received from the first RTD and the second RTD to calculate a differential voltage for each of the plurality of experiments, and (ii) convert the differential voltage into a digital signal;
   a processing unit that is configured to process the digital signal to detect explosive trace in the desorbed vapor, said processing unit comprising:
      a response processing module that is configured to subtract the differential voltage of each of the three or more experiments with the differential voltage of the subsequent experiment to obtain a processed response;
      a data processing module that is configured to (i) generate a graph for the processed responses, (ii) locate a position of minima, and (iii) calculate an area under the graph;

a data normalization module that is configured to calculate (a) a first slope, and (b) a second slope from the minima; and an explosive detection module that is configured to determine a presence of explosive trace in the desorbed vapor when (i) the first slope is greater than a first threshold slope, (ii) the second slope is greater than a second threshold slope, and (iii) the area under the graph is greater than a threshold area; and a display unit that is configured to display a status of one of (a) explosive trace is detected, or (b) no explosive trace is detected, wherein the processing unit determines (i) the specific voltage that is supplied to power the first micro-heater and the second micro-heater, and (ii) the constant current that is supplied to power the first RTD and the second RTD.

8. The system of claim 7, wherein the system comprises:

a plurality of nanowires that is configured to collect a vapor from a plurality of surfaces; and a heating element that is configured to heat the vapor to a temperature ranging from 60° C. to 100° C. to obtain the desorbed vapor.

9. A method of detecting explosive trace in a sample, comprising:

receiving a sample into a detection unit for detecting explosive trace;

supplying a specific voltage to a first heater and a second heater for a plurality of experiments;

supplying a constant current to a first RTD and a second RTD;

measuring changes in resistance of the first RTD and the second RTD due to heating of the first heater and the second heater to calculate voltages across the first RTD and the second RTD;

amplifying the voltages received from the first RTD and the second RTD to calculate a differential voltage for each of the plurality of experiments;

converting the differential voltage into a digital signal; and processing the digital signal to detect explosive trace in the sample, wherein said processing comprises:

subtracting the differential voltage of each of the three or more experiments with the differential voltage of the subsequent experiment to obtain a processed response;

generating a graph for the processed responses;

locating a position of minima;

calculating an area under the graph;

calculating (a) a first slope, and (b) a second slope from the minima; and determining a presence of explosive trace in the sample when (i) the first slope is greater than a first threshold slope, (ii) the second slope is greater than a second threshold slope, and (iii) the area under the graph is greater than a threshold area.

10. The method of claim 9, wherein the method comprises a step of displaying a status of one of (a) explosive trace is detected, or (b) no explosive trace is detected.

* * * * *